US007985601B2

(12) United States Patent
Healy et al.

(10) Patent No.: US 7,985,601 B2
(45) Date of Patent: Jul. 26, 2011

(54) TUNABLE, SEMI-INTERPENETRATING POLYMER NETWORKS (SIPNS) FOR MEDICINE AND BIOTECHNOLOGY

(75) Inventors: Kevin E. Healy, Moraga, CA (US); Ranee A. Stile, Highland Park, IL (US)

(73) Assignees: The Regents of the University of California, Oakland, CA (US); Northwestern University, Evanston, IL (US)

( * ) Notice: Subject to any disclaimer, the term of this patent is extended or adjusted under 35 U.S.C. 154(b) by 1337 days.

(21) Appl. No.: 10/385,900

(22) Filed: Mar. 10, 2003

(65) Prior Publication Data

US 2004/0001892 A1    Jan. 1, 2004

Related U.S. Application Data

(60) Provisional application No. 60/362,621, filed on Mar. 8, 2002.

(51) Int. Cl.
*G01N 33/544* (2006.01)
(52) U.S. Cl. ...... 436/535; 436/514; 436/528; 435/283.1
(58) Field of Classification Search .................. 524/555, 524/307; 424/486–489, 78, 425; 436/518, 436/535
See application file for complete search history.

(56) References Cited

U.S. PATENT DOCUMENTS

| | | | | |
|---|---|---|---|---|
| 5,219,564 | A * | 6/1993 | Zalipsky et al. | 424/78.17 |
| 5,334,640 | A * | 8/1994 | Desai et al. | 524/56 |
| 5,760,004 | A * | 6/1998 | Stedronsky | 514/21 |
| 6,224,893 | B1 * | 5/2001 | Langer et al. | 424/423 |
| 6,270,903 | B1 * | 8/2001 | Feng et al. | 428/429 |
| 6,639,014 | B2 * | 10/2003 | Pathak et al. | 525/90 |
| 2002/0007217 | A1 * | 1/2002 | Jacob et al. | 623/5.16 |
| 2007/0026518 | A1 * | 2/2007 | Healy et al. | 435/325 |

OTHER PUBLICATIONS

Sigma-Aldrich, Tutorial:Biocompatible/Biodegradable Materials, 2005, pp. 1-8.*
Gilanyi et al, Characterisation of monodisperse poly(N-Isopropylacrylamide) microgel particles, 2000, Phys Chem Chem Phys, 2, 1973-1977.*
Kao et al, Multifunctional poly(ethylene glycol) semi-interpenetrating polymer networks as highly selective adhesive substrates for bioadhesive peptide grafting, 1994, Biotech & Bioeng, 43,772-780.*
Miyata et al., Biomolecule-sensitive hydrogels, Jan. 2002, Adv Drug Deliv Rev; 54(1): p. 79-98.*
Stile et al., Poly(N-isopropylacrylamide)-based semi-interpenetrating polymer networks for tissue engineering applications. 1. effects of linear poly(acrylic acid) chains on phase behavior, 2002 Biomacromolecules, 3(3): pp. 591-600.*
Definition: bond, 1997, IUPAC Compendium of Chemical Terminology, 2nd Edition.*

(Continued)

*Primary Examiner* — N. C. Yang
(74) *Attorney, Agent, or Firm* — Morgan, Lewis & Bockius LLP; Jeffry S. Mann

(57) ABSTRACT

The present invention provides a class of semi-interpenetrating polymeric networks that include a linear polymer molecule functionalized with a bioactive moiety. The linear polymer is physically entangled within a matrix based upon a thermo-responsive polymer. The bioactive moiety is, e.g., a therapeutic moiety or a moiety that enhances the interaction of a cell with the polymer network. The polymer networks of the invention are flowable at room temperature, becoming solid or semi-solid at elevated temperatures (e.g., body temperature). The polymer networks are of use as drug delivery vehicles and as matrices for tissue engineering.

30 Claims, 8 Drawing Sheets

OTHER PUBLICATIONS

Definition: chemical bond, 2006, IUPAC Compendium of Chemical Terminology.*

Rudolph et al, Aluminium(III) hydration in aqueous solution. A raman spectroscopic investigation and an ab initio molecular orbital study of aluminium(III) water clusters, 2000, Phys Chem Chemic Phys, 2: pp. 5030-5040.*

Pauling, The nature of the chemical bond. Application of results obtained from the quantum mechanics and from a theory of paramagnetic susceptibility to the structure of molecules, 1931, Gates Chemical Laboratory, California Institute of Technology, 53: pp. 1367-1400.*

Steiner, 2002, The hydrogen bond in the solid state, 2002, Angew Chem Int Ed, 41: pp. 48-76.*

Horowitz et al., The role of oxygen dimmer in oxygen photolysis in the Herzberg continuum. A temperature dependence study, 1989, Am Chem Soc, 93(23): pp. 7959-7863.*

Freitas, Roberto S. et al.; "Temperature Sensitive Gels as Extraction Solvents"; *Chemical Eng. Sci*, 1987, vol. 42, No. 1, pp. 97-103.

Hoffman, Allan S. et al.; Thermally Reversible Hydrogels: II. Delivery and Selective Removal of Substances from Aqueous Solutions; *Journal of Controlled Release* 1988, vol. 4, pp. 213-222.

Lakhiari H. et al.; "Temperature-responsive size-exclusion chromatography using poly(N-isopropylacrylamide) grafted silica"; *Biochimica et Biophysica Acta* 1988, vol. 1379, pp. 303-313.

Monji, Nobuo et al.; "A Novel Immunoassay System and Bioseparation Process Based on Thermal Phase Separating Polymers"; *Applied Biochemistry and Biotechnology* 1987, vol. 14, pp. 107-120.

Okano, Teruo et al.; "A novel recovery system for cultured cells using plasma-treated polystyrene dishes grafted with poly(N-isopropylacrylamide)"; *Journal of Biomedical Materials Research* 1993, vol. 27, pp. 1243-1251.

Park, Tae Gwan et al.; "Immobilization of *Arthrobacter* simplex in Thermally Reversible Hydrogels: Effect of Gel Hydrophobicity on Steroid Conversion"; *Biotechnol*. 1991, vol. 7, pp. 383-390.

Shimizu, Shinichi et al.; "In Vitro Studies on a New Method for Islet Microencapsulation Using a Thermoreversible Gelation Polymer, N-Isopropylamide-Based Copolymer": *Artif. Organs* 1996, vol. 20, No. 11, pp. 1232-1237.

Stile, Ranee A. et al.; "Thermo-Responsive Peptide-Modified Hydrogels for Tissue Regeneration"; *Biomacromolecules* 2001, vol. 2, pp. 185-194.

Stile, Ranee A. et al.; "Peptide-Modified Thermoreversible Hydrogels for Tissue Regeneration"; *219th Book of Abstracts*, ACS National Meeting, Mar. 26-30, 2000.

Stile, Ranee A. et al.; "Synthesis and Characterization of Injectable Poly(N-isopropylacrylamide)-Based Hydrogels that support Tissue Formation In Vitro"; *Macromolecules* 1999, vol. 32, pp. 7370-7379.

Vakkalanka, Sarah K. et al.; "Temperature-and pH-sensitive terpolymers for modulated delivery of streptokinase"; *J. Biomater. Sci. Polymer Edn*. 1996, Vo. 8, No. 2, pp. 119-129.

Vernon, Brent; "Thermally Reversible Polymer Gels for Biohybrid Artificial Pancreas"; *Macromol. Symp*. 1996, vol. 109, pp. 155-167.

* cited by examiner

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: adhesion peptide from cell-binding domain of
      bone sialoprotein

<400> SEQUENCE: 1

Cys Gly Gly Asn Gly Glu Pro Arg Gly Asp Thr Tyr Arg Ala Tyr
1               5                   10                  15

<210> SEQ ID NO 2
```

```
<211> LENGTH: 10
<212> TYPE: PRT
<213> ORGANISM: Artificial Sequence
<220> FEATURE:
<223> OTHER INFORMATION: adhesion peptide from heparin-binding domain of
      bone sialoprotein

<400> SEQUENCE: 2

Cys Gly Gly Phe His Arg Arg Ile Lys Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: adhesion peptide motif

<400> SEQUENCE: 3

Phe His Arg Arg Ile Lys Ala
1               5

<210> SEQ ID NO 4
<211> LENGTH: 7
<212> TYPE: PRT
<213> ORGANISM: Artificial Sequence
<220> FEATURE:
<223> OTHER INFORMATION: peptide crosslinker cleavable by matrix
      metalloproteinase

<400> SEQUENCE: 4

Gln Pro Gln Gly Leu Ala Lys
1               5

<210> SEQ ID NO 5
<211> LENGTH: 10
<212> TYPE: PRT
<213> ORGANISM: Artificial Sequence
<220> FEATURE:
<223> OTHER INFORMATION: peptide that binds to hyaluronic acid

<400> SEQUENCE: 5

Lys Leu Lys Ser Gln Leu Val Lys Arg Lys
1               5                   10
```

US 7,985,601 B2

TUNABLE, SEMI-INTERPENETRATING POLYMER NETWORKS (SIPNS) FOR MEDICINE AND BIOTECHNOLOGY

CROSS-REFERENCES TO RELATED APPLICATIONS

This application is a non-provisional filing of U.S. Provisional Patent Application No. 60/362,621 filed on Mar. 8, 2002, the disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was supported in part by grant number R01 AR47304 from the NIH/NIAMS. The Government may have rights in the subject matter disclosed herein.

BACKGROUND OF THE INVENTION

Previously, poly (N-isopropylacrylamide) [p(NIPAAm)] homopolymer chains, copolymer chains, crosslinked hydrogels and p(NIPAAm)-based sIPNs (and also IPNs, which consist of two cross-linked networks that are physically entangled within each other but are not chemically connected in any way) have been studied for use in a number of diverse applications including solute recovery, (Freitas et al., *Chemical Engineering Science*, 42:97-103 (1987)) solute delivery, (Hoffman et al., *Journal of Controlled Release*, 4:213-222 (1986); Vakkalanka et al., *Journal of Biomaterials Science, Polymer Edition*, 8:119-129 (1996)) cell adhesion and manipulation, (Okano et al., *Journal of Biomedical Materials Research*, 27:1243-1251 (1993)) bioseparations, (Monji et al., *Applications in Biochemistry and Biotechnology*, 14:107-120 (1987)) catalytic reaction control, (Park et al., *Biotechnology Progress*, 7:383-390 (1991)) microencapsulation of cells, (Shimizu et al., *Artificial Organs*, 20:1232-1237 (1996)) chromatography, (Lakhiari et al., *Biochimica et Biophysica Acta*, 1379:303-313 (1998)) development of a biohybrid artificial pancreas, (Vernon et al., *Macromolecular Symposia*, 109:155-167 (1996)) and cell growth for tissue regeneration (Stile et al., *Biomacromolecules*, 2:185-194 (2001); Stile et al., *Abstracts of Papers of the American Chemical Society*, 219:584-POLY (2000); Stile et al., *Macromolecules*, 32:7370-7379 (1999)). The evolution of most of these applications was based on the unique phase behavior of p(NIPAAm) in aqueous media. The linear polymer chains (in the case of a sIPN) or the second network (in the case of an IPN) were added to the p(NIPAAm)-based hydrogels to change the swelling characteristics and/or the mechanical properties of the matrices. To our knowledge, there are no publications to date in which the polymer chains or the second network were modified with biomolecules to impart biological functionality to the sIPN or IPN.

Previous work has led to the development of injectable p(NIPAAm-co-AAc) hydrogels that demonstrated a phase transition slightly below body temperature, during which the rigidity of the matrix significantly increased. During in vitro culture, these matrices supported bovine articular chondrocyte viability and promoted the formation of tissue with histoarchitecture similar to that of native articular cartilage. Furthermore, when the AAc groups in the p(NIPAAm-co-AAc) hydrogel were functionalized with peptides containing relevant sequences found in ECM macromolecules, the peptide-modified hydrogels supported rat calvarial osteoblast viability, spreading, and proliferation. However, the procedure used to functionalize the hydrogels with the peptide sequences adversely altered the volume change characteristics of the hydrogels, significantly limiting the clinical utility of these matrices.

In view of the advantages of sIPNs and the deficiencies of prior sIPNs, a sIPN that could be functionalized to interact with cells on a molecular level, or to serve as a drug delivery vehicle while maintaining predictable and useful swelling properties would represent a significant advance in the art. Surprisingly, the present invention provides such a sIPN.

BRIEF SUMMARY OF THE INVENTION

It has now been discovered that sIPNs can be formed between a cross-linked thermo-responsive polymer and a linear polymer that is functionalized with a desired bioactive molecule. The sIPNs of the invention avoid the difficulties associated with prior sIPNs, providing a material with predictable and useful swelling properties.

Thus, in a first aspect, the present invention provides a semi-interpenetrating polymer network comprising: (a) a cross-linked thermo-responsive polymer; and (b) a linear polymer entangled within said cross-linked thermo-responsive polymer. The linear polymer is pre-derivatized with a bioactive molecule prior to combining the linear polymer and the thermo-responsive polymer.

The present invention also provides a method for preparing a semi-interpenetrating polymer network comprising a thermo-responsive polymer cross-linked with a cross-linking moiety; and a linear polymer entangled within said thermo-responsive polymer, said linear polymer derivatized with a biomolecule. The method includes:

(a) contacting the linear polymer with a monomeric precursor of the thermo-responsive polymer and a cross-linking agent;

(b) initiating polymerization of the monomeric precursor and the cross-linking moiety, thereby forming the semi-interpenetrating network; wherein (c) the semi-interpenetrating polymer network is protease degradable.

Other aspects, objects and advantages of the present invention will be apparent from the detailed description that follows.

DETAILED DESCRIPTION OF THE INVENTION

Abbreviations

Figure 1:
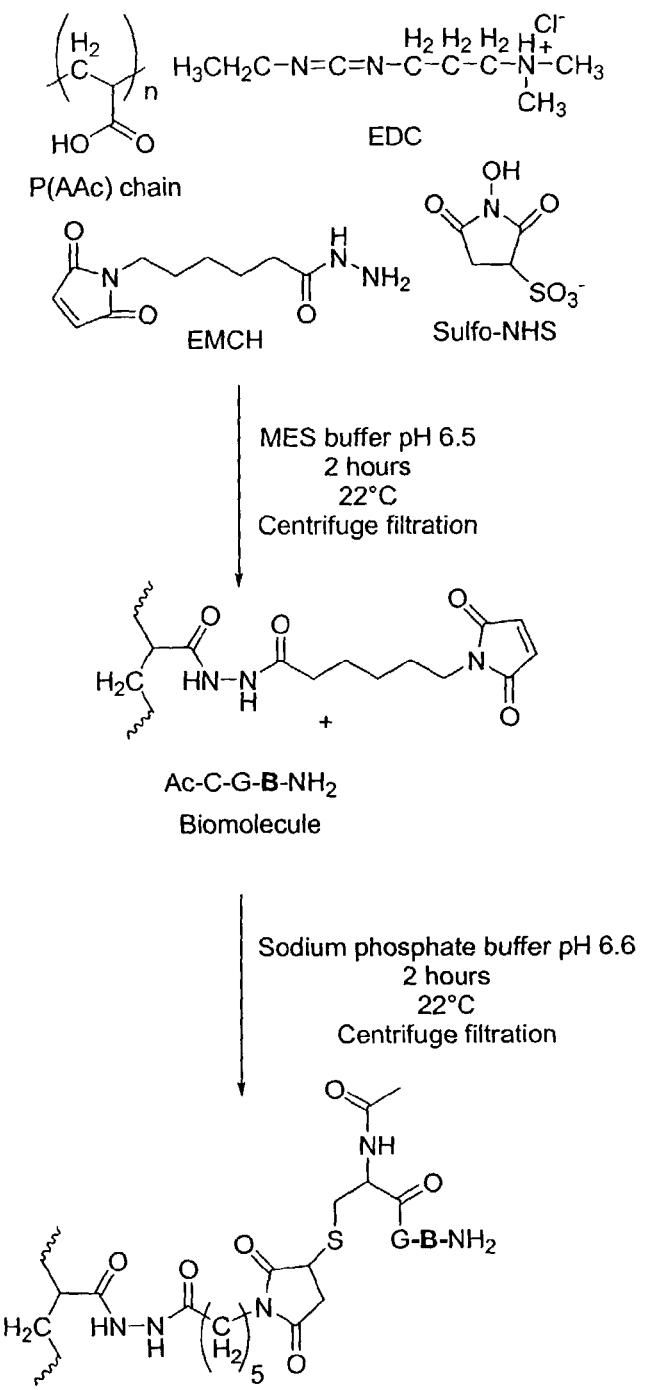
FIG. 1 is a scheme for preparing an exemplary modified linear polymer useful in a s-IPN of the invention in which p(AAc) is the linear polymer chain and a synthetic peptide serves as the biomolecule. The —COO⁻ groups in the linear p(AAc) chains are reacted with one end of a heterobifunctional cross-linker. The other end of the cross-linker is then used to graft the biomolecule to the p(AAc) chains.
Figure 2:
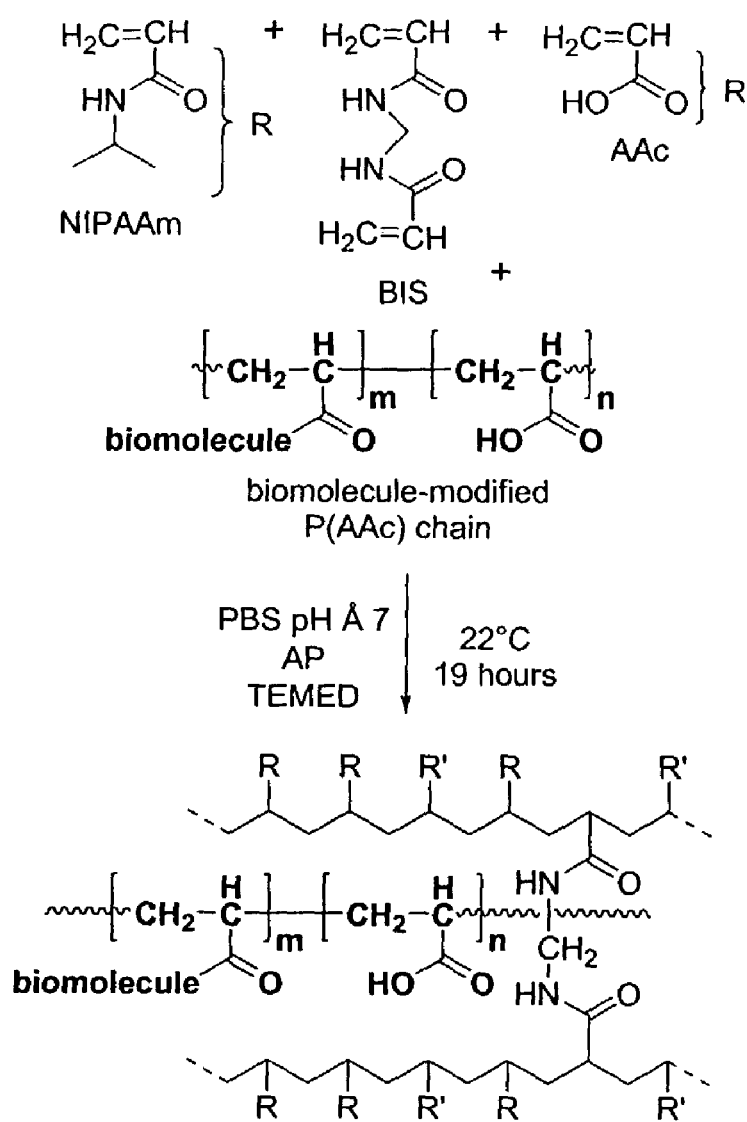
FIG. 2 is a synthetic scheme for preparing a s-IPN of the invention, which incorporates a biomolecule-modified linear p(AAc) polymer. The modified p(AAc) chains are added to the polymerization formulation, and the p(NIPAAm-co-AAc) cross-linked network forms in the presence of the chains. Thus, the chains are physically entangled within the network.
Figure 3:
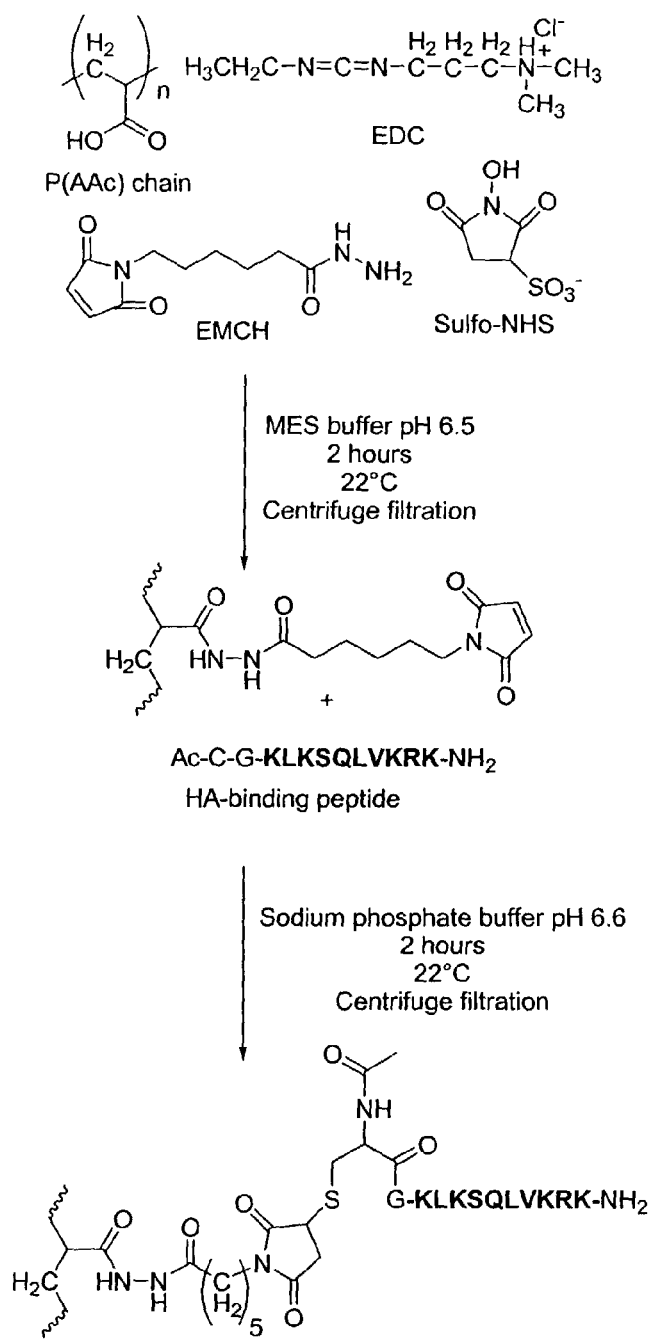
FIG. 3 is a scheme for preparing an exemplary modified linear polymer useful in a s-IPN of the invention in which p(AAc) is the linear polymer chain and a synthetic peptide serves as the biomolecule. The —COO⁻ groups in the linear p(AAc) chains are reacted with one end of a heterobifunctional cross-linker. The other end of the cross-linker is then used to graft the biomolecule to the p(AAc) chains. The specific synthetic peptide shown in FIG. 3 binds to hyaluronic acid (HA), for use in tissue adhesion applications.

As used herein, "NIPAAm," refers to "N-isopropylacrylamide."

The term "p(NIPAAm)," as used herein, refers to "poly(N-isopropylacrylamide)."

As used herein, "BIS," refers to "N,N'-methylenebisacrylamide."

The term, "AAc," as used herein, refers to "acrylic acid."

The term, "p(AAC)," as used herein, refers to linear "poly (acrylic acid)" chains.

The term, "p(NIPAAm-co-AAc)," as used herein, refers to a copolymer hydrogel formed from poly(N-isopropylacrylamide) and acrylic acid.

The term, "p(NIPAAm-co-AAc)-based sIPN," as used herein, refers to a sIPN formed from N-isopropylacrylamide-co-acrylic acid and a linear poly(acrylic acid).

The term, "p(NIPAAm)-based sIPN", as used herein, refers to a sIPN formed from N-isopropylacrylamide and a linear poly(acrylic acid).

"AP," as used herein, refers to "ammonium peroxydisulfate."

"TEMED," as used herein, refers to "N,N,N',N'-tetramethylethylenediamine."

"ECM," as used herein, refers to "extracellular matrix."

The term "sIPN," as used herein, refers to "semi-interpenetrating polymer network."

The term "EMCH," as used herein, refers to "N-ε-(maleimidocaproic acid)."

Definitions

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

"Antibody," as used herein, generally refers to a polypeptide comprising a framework region from an immunoglobulin or fragments or immunoconjugates thereof that specifically binds and recognizes an antigen. The recognized immunoglobulins include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

As used herein, "therapeutic moiety" means any agent useful for therapy including, but not limited to, antibiotics, anti-inflammatory agents, anti-tumor drugs, cytotoxins, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof.

As used herein, "a radioactive agent" includes any radioisotope which is effective in diagnosing or destroying a tumor. Examples include, but are not limited to, indium-111, cobalt-60. Additionally, naturally occurring radioactive elements such as uranium, radium, and thorium which typically represent mixtures of radioisotopes, are suitable examples of a radioactive agent. The metal ions are typically chelated with an organic chelating moiety.

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, intranasal or subcutaneous administration, or the implantation of a slow-release device e.g., a mini-osmotic pump, to the subject.

The term "isolated" refers to a material that is substantially or essentially free from components, which are used to produce the material. The lower end of the range of purity for the polymer networks is about 60%, about 70% or about 80% and the upper end of the range of purity is about 70%, about 80%, about 90% or more than about 90%.

"Hydrogel" refers to a water-insoluble and water-swellable cross-linked polymer that is capable of absorbing at least 10 times, preferably at least 100 times, its own weight of a liquid. "Hydrogel" and "thermo-responsive polymer" are used interchangeably herein.

The term "attached," as used herein encompasses interaction including, but not limited to, covalent bonding, ionic bonding, chemisorption, physisorption and combinations thereof.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

Introduction

The present invention embodies a platform technology consisting of a polymer matrix that aids in tissue formation ex vivo or tissue regeneration in vivo, drug or chemotherapy agent delivery, cell transplantation, and gene therapy. Ideally, these matrices deliver mammalian cells and/or therapeutic agents into the body and act as three-dimensional templates to support and promote tissue growth. The physical and chemical properties of hydrogels (polymers containing a significant volume of water) are exploited to mimic the native extracellular matrix surrounding mammalian cells, and these hydrogels serve to foster recapitulation of the tissue regeneration process. Exemplary semi-interpenetrating polymer networks (sIPNs) are composed of a cross-linked polymer network with entangled linear polymer chains. SIPNs are of use in a number of applications, including solute delivery and molecular separations.

The present invention provides sIPNs in which the cross-linked network is synthesized using a thermo-responsive polymer, such as poly(N-isopropylacrylamide) [p(NIPAAm)]. In addition, linear polymer chains, entangled within the thermo-responsive matrix are functionalized with bioactive molecules specific to the application of interest (e.g., tissue regeneration, tissue adhesion, controlling cell behavior, drug delivery, etc.). The linear polymer chains can be any macromolecule that is amenable to conjugation (e.g., containing COOH, SH, and $NH_2$ functional groups) with a biomolecule and does not affect the phase behavior of the thermo-responsive matrix (e.g., lower critical solution temperature and volume change).

Thus, in a first aspect, the present invention provides a semi-interpenetrating polymer network comprising: (a) a cross-linked thermo-responsive polymer; and (b) a linear polymer entangled within said cross-linked thermo-responsive polymer, said linear polymer derivatized with a bioactive molecule.

The crosslinked s-IPNs are extremely pliable and fluid-like at room temperature (RT), but demonstrate a phase transition as the matrix warms from RT to body temperature, yielding more rigid structures. Thus, the s-IPNs offer the benefit of in situ stabilization without the potential adverse effects of in situ polymerization (e.g., residual monomers, initiators, catalysts, etc.). The s-IPNs of the invention are preferably injectable through a syringe with about a 2 mm-diameter aperture without appreciable macroscopic fracture, support cell proliferation in vitro when seeded with cells, e.g., bovine articular chondrocytes or rat calvarial osteoblasts, and are also amenable to functionalization with bioactive molecules that interact with cell surface receptors.

The sIPNs of the invention are tunable in terms of their delivery, drug dosing, and mechanical and biochemical properties. The sIPNs of the invention are preferably deployed by minimally invasive methods, so at room temperature (i.e., ≈20-27° C.) these loosely-crosslinked networks are flowable, i.e., injectable through a small diameter aperture (from about 1 mm in diameter to about 5 mm in diameter) and do not exhibit macroscopic fracture following injection.

In an exemplary embodiment, the thermo-responsive polymer-based hydrogels are synthesized by simultaneously polymerizing and cross-linking N-isopropylacrylamide (NIPAAm) and acrylic acid (AAc) [p(NIPAAm-co-AAc) hydrogels]. To synthesize the sIPNs, these methods were modified by adding linear p(AAc) chains during the hydrogel formation. Due to the presence of the p(NIPAAm), the sIPNs demonstrate a significant increase in complex modulus (i.e., rigidity) when heated to body temperature, without exhibiting a significant change in either volume or water content.

In a preferred embodiment, the phase transition of p(NIPAAm) is exploited as a means for minimally invasive delivery of mammalian cells, macromolecules, chemotherapy agents, DNA and other drugs in a site-directed manner to a target area. The mechanical properties of the matrix can be readily altered by the addition of increased cross-links, by varying the NIPAAm:AAc molar ratio in the p(NIPAAm-co-AAc) hydrogel, or by varying the mass of the linear polymer in the sIPN. Furthermore, the sIPN fabrication is modular, in that functionalization of the linear polymer chains takes place prior to the sIPN synthesis, thereby allowing purification and the ability to create admixtures of distinct "macromolecular building blocks." The sIPNs of the invention have enormous potential in the fields of tissue engineering, chemotherapy, drug delivery, cell transplantation, interventional cardiology and radiology, orthopedic and maxillofacial surgery, and gene therapy.

The Polymers

Much of the discussion herein is focused on a sIPN, which is based upon a thermo-responsive polymer of (NIPAAm) and acrylic acid (AAc) [p(NIPAAm-co-AAc) hydrogels]. The focus of the discussion is for clarity of illustration and does not imply that the invention is limited to this exemplary sIPN.

The properties of the sIPNs of the invention are readily varied by altering the composition of the sIPN. The structure of the polymerizable monomer and the amount and structure of the cross-linking agent in the thermo-responsive polymer can be varied to alter the properties of the thermo-responsive polymer matrix. For example, the hydrophobicity/hydrophilicity ratio of the matrix can be varied by altering the hydrophobicity and hydrophilicity of the polymerizable monomers.

The Thermo-Responsive Polymer

The properties of the thermoresponsive polymer can be varied by choice of monomer(s), cross-linking agent and degree of polymer cross-linking. An exemplary variation in the monomer properties is hydrophobicity/hydrophilicity.

In general, providing larger hydrophobic moieties on a thermo-responsive polymer decreases water swellability. For example, hydrogels made of isopropyl acrylamide are water swellable and possess small hydrophobic moieties (i.e., an isopropyl group). The hydrophobic binding character of these gels is salt dependent. However, when the isopropyl group is replaced by a larger hydrophobic moiety, e.g., an octyl group, the gel loses some of its water swellability.

Exemplary hydrophilic moieties are derived from monomers that include N-methacryloyl-tris(hydroxymethyl)methylamine, hydroxyethyl acrylamide, hydroxypropyl methacrylamide, N-acrylamido-1-deoxysorbitol, hydroxyethylmethacrylate, hydroxypropylacrylate, hydroxyphenylmethacrylate, poly(ethylene glycol)monomethacrylate, poly(ethylene glycol) dimethacrylate, acrylamide, glycerol monomethacrylate, 2-hydroxypropyl acrylate, 4-hydroxybutyl methacrylate, 2-methacryloxyethyl glucoside, poly(ethyleneglycol) monomethyl ether monomethacrylate, vinyl 4-hydroxybutyl ether, and derivatives thereof.

Presently preferred hydrophilic moieties are derived from monomers that include a poly(oxyalkylene) group within their structure. Poly(ethylene glycol)-containing monomers are particularly preferred.

Presently preferred hydrophobic moieties are derived from acrylamide monomers in which the amine nitrogen of the amide group is substituted with one or more alkyl residues.

Exemplary hydrophobic moieties are derived from monomers selected from N-isopropylacrylamide, N,N-dimethylacrylamide, N,N-diethyl(meth)acrylamide, N-methyl methacrylamide, N-ethylmethacrylamide, N-propylacrylamide, N-butylacrylamide, N-octyl (meth)acrylamide, N-dodecylmethacrylamide, N-octadecylacrylamide, propyl(meth)acrylate, decyl(meth)acrylate, stearyl(meth)acrylate, octyl-triphenylmethylacrylamide, butyl-triphenylmethylacrylamide, octadedcyl-triphenylmethylacrylamide, phenyl-triphenylmethylacrlamide, benzyl-triphenylmethylacrylamide, and derivatives thereof.

The Linear Polymer

Similar to the thermo-responsive polymer, the hydrophobicity/hydrophilicity of the linear polymer can be varied. Moreover, characteristics of the polymer such as length and number and identity of reactive functional groups can be varied as desired for a particular application.

Useful linear polymer chains include any long-chain polymer that contains a functional group (e.g., $-NH_2$, $-COO^-$, $-SH$, etc.) that is amenable to modification with biomolecules. Examples of such linear polymers are hyaluronic acid (HA), poly(methacrylic acid), poly(ethylene glycol)(EG), or poly(lysine). The linear polymer chain can also be a copolymer, e.g. p(AAc-co-EG) or a terpolymer. The only requirement for the linear chain is that it is amenable to either grafting biological molecules or particles, e.g., for gene therapy and does not interfere with the phase change properties of the cross-linked network.

Another exemplary class of linear polymers include any long-chain polymer that contains functional groups (e.g., aldehydes, etc) that can interact nonspecifically with the amines in tissues or components in the ECM. Examples of such linear polymers that can be modified with aldehyde groups are hyaluronic acid (HA), poly(methacrylic acid), poly(ethylene glycol)(EG), or poly(lysine). The linear polymer chain can also be a copolymer, e.g. p(AAc-co-EG) or a terpolymer.

Another exemplary class of linear polymers are electrically-responsive polymers for fostering growth of electrically-responsive cells such as cardiac myocytes or neurons. In addition to p(AAc), linear chains of poly(methacrylic acid), poly(dimethyl-aminopropylacrylamide), poly(2-acrylamido-2-methylpropane sulphonic acid), HA, copolymers of these polymers, and other electro-responsive linear polymers that change their shape under an electric field or potential can be incorporated into the sIPN. These chains can be additionally functionalized with biomolecules to make an electrically and bioactive hydrogel capable of stimulating cell growth and alignment. The cellular alignment is caused by the templating of the cells on the aligned electrically active linear polymer chains.

In addition to linear polymers, branched polymers, such as commercially available poly(EG) derivatives (e.g., Shearwater Polymers, Huntsville, Ala.), can also be used.

The Bioactive Molecule

In exemplary embodiments, the polymer network includes a bioactive biomolecule, e.g., functional protein, enzyme, antigen, antibody, peptide, nucleic acid (e.g., single nucleotides or nucleosides, oligonucleotides, polynucleotides and single- and higher-stranded nucleic acids), lectin, receptor, saccharide, ganglioside, cerebroside or a combination thereof.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal.

Bioactive molecules of use in the compositions of the present invention include natural and modified biomolecules and therapeutic moieties. The discussion that follows focuses on the use of a peptide as an exemplary bioactive molecule. The focus is for clarity of illustration only. It will be apparent to those of skill in the art that substantially any bioactive molecule can be incorporated into the compositions of the invention.

Exemplary peptides that can be utilized in forming the compositions of the invention are set forth in Table 1.

TABLE 1

| HormonesandGrowthFactors | ReceptorsandChimericReceptors |
|---|---|
| G-CSF | CD4 |
| GM-CSF | Tumor Necrosis Factor (TNF) receptor |
| TPO | Alpha-CD20 |
| EPO | MAb-CD20 |
| EPO variants | MAb-alpha-CD3 |
| alpha-TNF | MAb-TNF receptor |
| Leptin | MAb-CD4 |
| VEGF (all isoforms) | PSGL-1 |
| Sonic hedgehog (Shh) | MAb-PSGL-1 |
| EnzymesandInhibitors | Complement |
| t-PA | GlyCAM or its chimera |
| t-PA variants | N-CAM or its chimera |
| Urokinase | MonoclonalAntibodies(Immunoglobulins) |
| Factors VII, VIII, IX, X | MAb-anti-RSV |
| Dnase | MAb-anti-IL-2 receptor |
| Glucocerebrosidase | MAb-anti-CEA |
| Hirudin | MAb-anti-platelet IIb/IIIa receptor |
| α1 antitrypsin | MAb-anti-EGF |
| Antithrombin III | MAb-anti-Her-2 receptor |
| CytokinesandChimericCytokines | Cells |
| Interleukin-1 (IL-1), 1B, 2, 3, 4 | Red blood cells |
| Interferon-alpha (IFN-alpha) | White blood cells (e.g., T cells, B cells, |
| IFN-alpha-2b | dendritic cells, macrophages, NK cells, |
| IFN-beta | neutrophils, monocytes and the like |
| IFN-gamma | Stem cells |
| Chimeric diptheria toxin-IL-2 | Bone marrow derived stem cells |
|  | C-kit+ bone marrow derived cells |

Other exemplary peptides useful in the composition of the invention include members of the immunoglobulin family (e.g., antibodies, MHC molecules, T cell receptors, and the like), intercellular receptors (e.g., integrins, receptors for hormones or growth factors and the like) lectins, and cytokines (e.g., interleukins). Additional examples include tissue-type plasminogen activator (t-PA), renin, clotting factors such as factor VIII and factor IX, bombesin, thrombin, hematopoietic growth factor, colony stimulating factors, viral antigens, complement proteins, α1-antitrypsin, erythropoietin, P-selectin glycopeptide ligand-1(PSGL-1), granulocyte-macrophage colony stimulating factor, anti-thrombin III, interleukins, interferons, proteins A and C, fibrinogen, herceptin, leptin, glycosidases, among many others. This list of polypeptides is exemplary, not exclusive. The sIPN of the invention can also include a chimeric protein, including, but not limited to, chimeric proteins that include a moiety derived from an immunoglobulin, such as IgG.

In an exemplary embodiment, the invention provides a hydrogel to stimulate bone formation incorporating the adhesion peptides acetyl-CGGNGEPRGDTYRAY-NH$_2$ (SEQ ID NO: 1) (-RGD-) and acetyl-CGGFHRRIKA-NH$_2$ (SEQ ID NO: 2) (-FHRRIKA-) (SEQ ID NO: 3), selected from the cell-binding and heparin-binding domains of bone sialoprotein (BSP), to accelerate proliferation of primary rat calvaria osteoblast-like (RCO) cells in contact with the peptide modified p(NIPAAm-co-AAc) hydrogels.

Both naturally-derived and synthetic peptides and nucleic acids are of use in conjunction with the present invention; these molecules can be attached to a component of the sIPN or a crosslinking agent by any available reactive group. For example, peptides can be conjugated through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

Therapeutic Moieties

In another exemplary embodiment, the linear polymer includes a therapeutic moiety. The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities.

In certain embodiments, the therapeutic moieties are inactive when attached to the polymer. Cleavage from the polymer restores activity.

Classes of useful therapeutic moieties include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, caramiphen and carbetapentane); antipruritic drugs (e.g., methdilazine and trimeprazine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyramide, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltiazem, amiodarone, isoxsuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chloroprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin.

The therapeutic moiety can also be a hormone (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone); modulators of diabetes (e.g., glyburide or chlorpropamide); anabolics, such as testolactone or stanozolol; androgens (e.g., methyltestosterone, testosterone or fluoxymesterone); antidiuretics (e.g., desmopressin); and calcitonins.

Also of use in the present invention are estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

Conjugation of Bioactive Molecules to Linear Polymer

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

The therapeutic moiety is attached to the linear polymer either directly or through a cross-linking agent. Either of these modes of attachment can be engineered to produce a linkage that is either stable under biologically relevant conditions, or which is cleaved under selected conditions, releasing the bioactive agent from the matrix.

In general, the linear polymer and the bioactive molecule are linked together through the use of reactive groups, which are typically transformed by the linking process into a new organic functional group or unreactive species. The reactive functional group(s) are located at any position of the bioactive molecule and the linear polymer. Reactive groups and classes of reactions useful in practicing the present invention are generally those that are well known in the art of bioconjugate chemistry. Currently favored classes of reactions available with reactive species are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Methods and chemistry for activating polymers as well as methods for conjugating bioactive molecules onto polymers are described in the literature. See, R. F. Taylor, (1991), PROTEIN IMMOBILISATION. FUNDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); and Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Useful reactive functional groups pendent from a linear polymer or bioactive molecule include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the sIPN or its components. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In an exemplary embodiment, the therapeutic moiety is attached to the remainder of the linear polymer via a linkage that is cleaved under selected conditions. Exemplary conditions include, but are not limited to, a selected pH (e.g., stomach, intestine, endocytotic vacuole), the presence of an active enzyme (e.g, esterase, reductase, oxidase), light, heat and the like. Many cleaveable groups are known in the art. See, for example, Jung et al., *Biochem. Biophys. Acta*, 761: 152-162 (1983); Joshi et al., *J Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J Immunol.*, 143: 1859-1867 (1989).

The discussion above is also relevant to the formation of the thermo-responsive polymer: the polymerizable monomers and cross-linking agents can include one or more of the reactive groups discussed therein. Moreover, the thermo-responsive polymer can include one or more degradable, or non-degradable bond or cross-linkers without limitation on the structure of the bond or linker.

Cross-Linking Groups

Cross-linking groups are useful to form the cross-links in the thermo-responsive polymer matrix and to attach the bioactive molecule to the linear polymer. The discussion that follows is relevant to both types of cross-linking interactions: bioactive molecules cross-linked to the linear polymer; and cross-links within the thermoresponsive polymer.

Both the amount and the identity of the cross-linking agent used in the embodiments of the present invention are variable without limitation. For example, the amount of the cross-linking agent with respect to the polymerizable monomers can vary and it is well within the abilities of one of skill in the art to determine an appropriate amount of cross-linking agent to form a hydrogel having desired characteristics. In an exemplary embodiment, the cross-linking agent is used in an amount ranging preferably from 0.0001 weight parts to 10 weight parts, more preferably from 0.001 weight parts to 5 weight parts, most preferably from 0.01 weight parts to 2 weight parts, based on 100 parts by weight of either the hydrophobic or hydrophilic monomer.

Exemplary bifunctional compounds which can be used in the present invention include, but are not limited to, bifunctional poly(ethyleneglycols), polyamides, polyethers, polyesters and the like. General approaches for cross-linking two components are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are discussed as components of the linear polymer. The focus of the discussion is for clarity of illustration. Those of skill in the art will appreciate that the discussion is relevant to reactive groups on the bioactive molecule as well.

In an exemplary strategy for species that contain thiol groups (e.g., proteins or synthetic peptides containing cysteine residues), the —SH groups are grafted to the —COO$^-$ groups of, e.g., the p(AAc) chains using the cross-linker N-$\epsilon$-(maleimidocaproic acid) hydrazide (EMCH; Pierce, Rockford, Ill.). The hydrazide end of EMCH is first reacted with the —COO⁻ groups in the p(AAc) chains using a dehydration agent such as, 1-ethyl-3-(3-dimethylaminopropyl) carbodiimide in the presence of N-hydroxysulfosuccinimide in 2-(N-morpholino) ethanesulfonic acid. The unreacted components are removed via dialysis, the product is lyophylized, and then the maleimide end of EMCH is reacted with the —SH groups of the biomolecule in sodium phosphate buffer (pH 6.6) (FIG. 1).

Another exemplary strategy involves incorporation of a protected sulfhydryl onto the polymer chain using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the properties of the linear polymer, there is an array of other crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the amine-containing molecule. SATA also reacts with primary amines, but incorporates a protected sulfhydryl, which is later deacetylated using hydroxylamine to produce a free sulfhydryl. In each case, the incorporated sulfhydryl is free to react with other sulfhydryls or protected sulfhydryl, like SPDP, forming the required disulfide bond.

The above-described strategies are exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide) and TPMPH (S-(2-thiopyridyl) mercapto-propionohydrazide) react with aldehydes, thus forming a hydrazone bond between the hydrazide portion of the crosslinker and the periodate generated aldehydes. TPCH and TPMPH introduce a 2-pyridylthione protected sulfhydryl group onto a species, which can be deprotected with DTT and then subsequently used for conjugation, such as forming disulfide bonds between components.

If disulfide bonding is found unsuitable for producing stable linear polymers, other crosslinkers may be used that incorporate more stable bonds between components. The heterobifunctional crosslinkers GMBS ((N-gamma-maleimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the linear polymer to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and linear polymer production.

A variety of reagents are used to modify the components of the linear polymer with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

i. Preferred Specific Sites in Crosslinking Reagents

1. Amino-Reactive Groups

In one preferred embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a sIPN component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the sIPN components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the sIPN components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of sIPN components, but also with sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of the linear polymer or components of the thermo-responsive polymer. Although unstable Schiff bases are formed upon reaction of the amino groups with the aldehydes of the aldehydes, glutaraldehyde is capable of modifying a component of the sIPN with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the sIPN components, but reaction with the amino groups is the most important, resulting in a stable sulfonamide linkage.

2. Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the sIPN components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage (Yamada et al., *Biochemistry* 20: 4836-4842, 1981).

ii. Preferred Nonspecific Sites in Crosslinking Reagents

In addition to the use of site-specific reactive moieties, the present invention contemplates the use of non-specific reactive groups to link together two components of the sIPN.

Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wave length. Unsubstituted arylazides have an absorption maximum in the range of 260-280 nm, while hydroxy and nitroarylazides absorb significant light beyond 305 nm. Therefore, hydroxy and nitroarylazides are most preferable since they employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

iii. Homobifunctional Reagents

1. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOES), ethylene glycol-bis(succinimidylsuccinate) (EGS), ethylene glycolbis(sulfosuccinimidylsuccinate) (sulfo-EGS), dithiobis (succinimidyl-propionate) (DSP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-3,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, (α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-p-(4-azidosalicylamido)ethyldisulfide (BASED), di-N-(2-nitro-4-azidophenyl)-cystamine-S,S-dioxide (DNCO), and 4,4'-dithiobisphenylazide.

iv. HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature.

Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino) hexanoylamino)hexanoate (SIAXX), succinimidyl-6-(((4-(iodoacetyl)-amino)-methyl)-cyclohexane-1-carbonyl) aminohexanoate (SIACX), and succinimidyl-4((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety for primary amino groups is defined by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art (see, for example, Pomato et al., U.S. Pat. No. 5,965,106). It is within the abilities of one of skill in the art to chose an appropriate cross-linking agent for a particular application.

v. Cleavable Linker Groups

In yet a further embodiment, the linker group is provided with a group that can be cleaved to dissociate the two cross-linked species. Many cleaveable groups are known in the art. See, for example, Jung et al., *Biochem. Biophys. Acta* 761: 152-162 (1983); Joshi et al., *J Biol. Chem.* 265: 14518-14525 (1990); Zarling et al., *J. Immunol.* 124: 913-920 (1980); Bouizar et al., *Eur. J Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups are commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to their being endocytized (e.g., cis-aconityl; see, Shen et al., *Biochem. Biophys. Res. Com-* mun. 102: 1048 (1991)). Preferred cleaveable groups comprise a cleaveable moiety which is a member selected from the group consisting of disulfide, ester, imide, carbonate, nitrobenzyl, phenacyl and benzoin groups.

In yet another exemplary embodiment, the sIPN of the invention are used in the context of the natural process of proteolytic remodeling of the extracellular matrix, which is essential in tissue morphogenesis during fetal development, inflammation, arthritis, cancer, wound healing, and tissue regeneration (Massova et al., *FASEB Journal*, 12:1075-1095 (1998); Johansson et al., *Developmental Dynamics*, 208:387-397 (1997)). To make the hydrogel scaffolds degradable oligopeptide crosslinkers that are specifically cleaved by the matrix metalloproteinase (MMP) family are incorporated into the sIPNs. MMP's are a structurally and functionally related family of zinc-dependent endopeptidases that cleave either one or several ECM proteins (Massova et al., *FASEB Journal*, 12:1075-1095 (1998)). Recently, West and Hubbell (West et al., *Macromolecules*, 32:241-244 (1999)) developed a new class of telechelic biodegradable block copolymers that when synthesized into a crosslinked hydrogel were specifically degraded by either plasmin or crude collagenase. Thus, the feasibility of protease degradation of oligopeptide crosslinked hydrogels has been demonstrated in vitro (West et al., *Macromolecules*, 32:241-244 (1999)).

An exemplary embodiment of the invention is a sIPN that supports bone formation, which incorporates peptide crosslinkers that mimic the domain on type II collagen that is cleaved by collagenase-3 (MMP-13). The choice of peptides that model collagen type II is based on the concept that during endochondral bone formation, a cartilage matrix template, rich in collagen type II, is remodeled and replaced by bone, (Bilezikian et al., Eds., *Principles of Bone Biology* (Academic Press, Inc., San Diego, Calif., 1996)) and that osteoblasts synthesize MMP-13, a type II collagen specific MMP. The substrate specificity of MMP-13 was demonstrated by its ability to degrade type II collagen six times more effectively than either collagen type I or III, and its nearly a 50-fold stronger collagenolytic activity than either MMP-1 or MMP-8 (Mitchell et al., *Journal of Clinical Investigation*, 97:761-768 (1996); Knauper et al., *Journal of Biological Chemistry*, 271:1544-1550 (1996)). In addition, the expression of MMP-13 appears to be limited to hypertrophic chondrocytes, periosteal cells, and osteoblasts during human fetal bone development (Johansson et al., *Developmental Dynamics*, 208:387-397 (1997)). However, MMP-13 has also been detected in human breast carcinoma tissue (Freije et al., *Journal of Biological Chemistry*, 269:16766-16773 (1994)) and in osteoarthritic cartilage and chondrocytes (Mitchell et al., *Journal of Clinical Investigation*, 97:761-768 (1996)). The limited expression of MMP-13 and its specificity for collagen type II make oligopeptides based on the cleavage site of MMP-13 ideal candidates for peptide crosslinkers in p(NIPAAm-co-AAc) hydrogels. Since MMP-13 has primary, secondary, and tertiary cleavage sites for type II collagen, all with different enzyme-substrate affinity ($K_M$) and maximal catalytic rate when the substrate is saturated ($k_{cat}$), (Mitchell et al., *Journal of Clinical Investigation*, 97:761-768 (1996)) then theoretically the degradation rate of the hydrogel could be tailored by selecting peptides with the appropriate cleavage site.

In an exemplary embodiment, the sIPN of the invention includes peptide crosslinkers (see, Table 2) as homogeneous components of the hydrogels. The degradation rates of the sIPNs with peptide crosslinkers can be altered by making hydrogels with mixed crosslinkers with different cleavage sites for MMP-13, e.g. primary versus tertiary sites, by changing the crosslinker density, and by changing substrate length or amino acids flanking the cleavage site (West et al., *Macromolecules*, 32:241-244 (1999); Netzel-Arnett et al., *Journal of Biological Chemistry*, 266:6747-6755 (1991)). The aforementioned modifications to the hydrogels alter the degradation rates by changing $k_{cat}/K_M$, an index of substrate specificity.

Sequences of peptide crosslinkers proposed for the proteolytically degradable p(NIPAAm-co-AAc) hydrogels are displayed in Table 2. The sequences are based on collagenase peptide substrates, modeled from human type II collagen, defined in the literature (Mitchell et al., *Journal of Clinical Investigation*, 97:761-768 (1996)). Values for the enzyme kinetic parameters are given for the primary cleavage site even though the data represent the cumulative activity of all cleavage sites.

Table 2

| Peptide Crosslinker | Cleavage Site | Enzyme | $K_M$ (µM) | $k_{cat}$ (h$^{-1}$) | $k_{cat}/K_M$ (µM$^{-1}$ h$^{-1}$) |
|---|---|---|---|---|---|
| GPQGLAG | 1°, Gly$^{906}$-Leu$^{907}$ | MMP-1 (H) | 1-2.1 | 2 – 1 | 0.5-2 |
| GPQGLAG | 1°, Gly$^{906}$-Leu$^{907}$ | MMP-13 (H) | 2 | 23 | 11.5 |
| GPQGLAG | 1°, Gly$^{906}$-Leu$^{907}$ | MMP-13 (R) | 0.9 | 14.2 | 15.7 |
| LAGQRG | 2°, Gly$^{909}$-Gln$^{910}$ | MMP-13 (H) | | | <11.5 |
| QRGIVG | 3°, Gly$^{912}$-Ile$^{913}$ | MMP-13 (H) | | | <11.5 |

$k_{cat}$ is expressed as molecules of type II collagen cleaved/molecule of collagenase/hour
H: human; R: rat Peptide crosslinkers can be synthesized on a commercial peptide synthesizer, purified, and verified to be >97% pure by HPLC and mass spectroscopy. The peptides are synthesized using standard methods with side group protection. Protection of the amine groups is critical since it is important for the docking of the MMP-13 to the peptide substrate (Mitchell et al., *Journal of Clinical Investigation*, 97:761-768 (1996)). To acrylate the peptides, while still on the resin, the Fmoc protection group from the N terminus is cleaved with 20% piperidine in dimethylformamide (DMF) and the free amine is acrylated by reacting acrylic acid with 1-ethyl-3-(3-dimethylaminopropyl) carbodiimide (EDC, Pierce, Rockford, Ill., USA) with the $NH_2$ in a similar manner to that described previously by Bearinger et al. (Bearinger et al., *Journal of Biomaterials Science, Polymer Edition*, 9:629-52 (1998)). Briefly, the carboxylic acid on the acrylic acid is linked to the N terminal amine by inducing a carbodiimide reaction utilizing 0.400 mg/ml EDC and 1.100 mg/ml N-Hydroxysulfosuccinimide (Sulfo-NHS, Pierce) in 2-(N-Morpholino) ethanesulfonic acid, 0.100 M, in 0.5 M NaCl conjugation buffer (MES, Pierce) at a pH of 6.0. Although this pH is low, it is not nearly low enough to cleave the peptide off the resin or remove side chain protection. The reaction proceeds for 1 h, and then the resin is rinsed with 10% TFA to cleave the peptide from the resin with side group protection in tact. The carboxyl termini is acrylated in solution by reacting the —COOH with ethylenediamine with EDC (similar conditions as above) to generate a free amine and then following the reaction scheme outlined above for coupling acrylic acid with the —$NH_2$.

To synthesize the sIPN hydrogels, the synthetic route and conditions for polymerization for the non-degradable sIPN hydrogels is used, replacing the non-degradable crosslinker with the peptide crosslinkers. The side chain protection groups on the cross-linkers are deprotected, e.g., with 90% TFA prior to synthesis. Degradable hydrogels synthesized as described above can be used in a similar manner to the non-degradable gels; however, the scaffold will be temporary based on the enzymatic cleavage of the cross-links.

Purification

The products produced by the above processes can be used without purification. However, it is usually preferred to recover the product. For components of the composition that are soluble, standard, well known techniques for recovery of polymers such as thin or thick layer chromatography, column chromatography, ion exchange chromatography, gel permeation chromatography or membrane filtration can be used.

For insoluble components, membrane filtration can be used. Exemplary methods of membrane filtration include nanofiltration or reverse osmosis. For instance, membrane filtration can be used to remove unreacted or incompletely reacted monomers and oligomers. Nanofiltration or reverse osmosis can be used to remove salts and/or purify the products. Nanofilter membranes are a class of reverse osmosis membranes which pass monovalent salts but retain polyvalent salts and uncharged solutes larger than about 100 to about 2,000 Daltons, depending upon the membrane used. Thus, in a typical application, sIPNs prepared by the methods of the present invention will be retained in the membrane and contaminating salts will pass through.

Other methods of purifying the sIPNs of the invention include extraction methods utilizing aqueous solvents, organic solvents and combinations thereof. If the sIPN results in the formation of a solid, the particulate material is removed, for example, by centrifugation or ultrafiltration.

Other methods of purification of sIPNs of the invention that are derivatized with a bioactive molecule include, e.g., immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

A protease inhibitor, e.g., methylsulfonylfluoride (PMSF) may be included in any of the foregoing steps to inhibit proteolysis and antibiotics may be included to prevent the growth of adventitious contaminants.

Pharmaceutical Compositions

In another aspect, the invention provides a pharmaceutical composition. The pharmaceutical composition includes a pharmaceutically acceptable diluent and a sIPN of the invention.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the sIPN of the invention can be incorporated into liposomes formed from standard vesicle-forming lipids. A variety of methods are available for preparing liposomes, as described in, e.g., Szoka et al., Ann. Rev. Biophys. Bioeng. 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

The Methods

The present invention also provides a method for preparing a semi-interpenetrating polymer network comprising a thermo-responsive polymer cross-linked with a cross-linking moiety; and a linear polymer entangled within said thermo-responsive polymer. The linear polymer is derivatized with a biomolecule. The method includes:

(a) contacting the linear polymer with a monomeric precursor of the thermo-responsive polymer and a cross-linking agent; and (b) initiating polymerization of the monomeric precursor and formation of the cross-linking moiety, thereby forming the semi-interpenetrating network; wherein (c) the semi-interpenetrating network is protease degradable.

In another embodiment, the invention provides a method in which the thermo-responsive polymer is prepared and dried. A mixture of the linear polymer-bioactive molecule conjugate is then added to the dried thermo-responsive polymer. The thermo-responsive polymer swells, thereby imbibing the functionalized linear polymer and forming the sIPN.

The materials, methods and devices of the present invention are further illustrated by the examples, which follow. These examples are offered to illustrate, but not to limit the claimed invention.

EXAMPLES

The present examples detail the formation of a s-IPN to stimulate bone formation incorporating the adhesion peptides acetyl-CGGNGEPRGDTYRAY-NH$_2$(-RGD) and acetyl-CGGFHRRIKA-NH$_2$(-FHRRIKA-), selected from the cell-binding and heparin-binding domains of bone sialoprotein (BSP), to accelerate proliferation of primary rat calvaria osteoblast-like (RCO) cells in contact with the peptide modified p(NIPAAm-co-AAc) hydrogels.

The materials used to synthesize the sIPN include the following: NIPAAm, AAc, N,N'-methylenebisacrylamide (BIS), ammonium peroxydisulfate (AP), N,N',N'-tetramethylethylenediamine (TEMED), and linear p(AAc) chains (450,000 g/mol, acid form), which were obtained from Polysciences, Inc. (Warrington, Pa.), and Dulbecco's Phosphate-Buffered Saline (PBS; 1.51 mM KH$_2$PO$_4$, 155 mM NaCl, and 2.7 mM Na$_2$HPO$_4$; without CaCl$_2$, without MgCl$_2$; pH=7.2±0.1), which was obtained from GIBCO BRL (Grand Island, N.Y.).

Example 1

The synthesis of the polymeric networks is separated into two parts: first the linear polymer chains are functionalized with a biomolecule of interest, and purified; second, the sIPN is synthesized with the bio-functionalized linear chains.

1.1 Synthesis of the Linear Chain

The hydrazide end of EMCH (0.5 g/mL) was first reacted with the —COO$^-$ groups in the p(AAc) chains (3 mg/mL) using 1-ethyl-3-(3-dimethylaminopropyl) carbodiimide (EDC; Pierce, 3.9 mg/mL) and N-hydroxysulfosuccinimide (Sulfo-NHS, Pierce, 1.1 mg/mL) in 2-(N-morpholino) ethanesulfonic acid, 0.9% NaCl, conjugation buffer (MES, Pierce, 0.1 M, pH 6.5) for 2 hours at 22° C. The unreacted components were removed via centrifugation, and then the maleimide end of EMCH was reacted with the —SH groups of the biomolecule in 0.1 M sodium phosphate buffer (pH 6.6) for 2 hours at 22° C. The unreacted components were removed via centrifugation, the product was lyophylized, and the functionalized p(AAc) chains were used to synthesize the semi-IPNs, as detailed below.

1.2 Preparation of the s-IPN

The functionalized p(AAc) chains (0.001 g to 0.013 g) were added to 2.4395 g (22 mmol) of NIPAAm, 0.005 g (0.0325 mmol) of BIS, 0.0605 g (0.84 mmol) of AAc, and 50 mL of PBS, and the mixture was bubbled with dry nitrogen gas in a two-neck flask for 15 minutes to remove dissolved oxygen. Following the nitrogen gas purge, 0.020 g (0.0876 mmol) of AP and 200 µL (1.3 mmol) of TEMED were added as the initiator and accelerator, respectively. The mixture was stirred vigorously for 15 s and allowed to polymerize at 22° C. for 19 h under regular fluorescent lighting in a 250 mL glass beaker covered with a glass plate. Following the polymerization, the p(NIPAAm-co-AAc)-based semi-IPN was washed three times, 15-20 minutes each, in excess ultrapure water (UPW, 18.2 MΩ cm) to remove unreacted compounds.

Example 2

The present invention identifies optimal conditions for matrix-assisted delivery of bone marrow derived Lin-c-kit+ cells into injured myocardium. Poly(N-isopropylacrylamide)-based {p(NIPAAm)-based} semi-interpenetrating polymer networks (sIPNs), consisting of p(NIPAAm)-based hydrogels and linear poly(acrylic acid) {p(AAc)} will be used as an artificial extracellular matrix to deliver concentrated populations of isolated Lin-c-kit+ bone marrow cells into infracted areas. These gels contain various ligands and act as a bioactive template/matrix to guide regeneration of myocardium and blood vessels.

2.1 Hydrogel Preparation

To demonstrate the utility of sIPNs as vehicles for matrix-assisted delivery of bone marrow derived Lin-c-kit+ cells into injured myocardium, a model sIPN with a fluorophore grafted to the linear pAAc chains was used to probe the position of the gel within the heart after injection.

2.2 Hydrogel Preparation

The fluorophore Alexa Fluor® 568 hydrazide (Molecular Probes, Eugene, Oreg.) has been covalently grafted to 450,000 g/mol chains of p(AAc). This was achieved with an overnight room temperature carbodiimide reaction in a solution of 5 g/L p(AAc), 0.13 mM Alexa Fluor hydrazide and 6.2 g/L 1-ethyl-3-[dimethylaminopropyl]carbodiimide hydrochloride in 0.1M MES buffer at pH 5.5. This reaction created a primary amide bond between hydrazide and the p(AAc) carboxylic acid sites. To purify the p(AAc) product, two successive filtrations were performed using 50 kDa-cutoff centrifugal filtration units. The resulting product was diluted, foamed and lyophilized to produce a fibrous "fluffy" product. This reaction scheme yielded a substitution efficiency of 6×10$^{-4}$ Alexa molecules per AAc monomer (with one carboxylic acid site per monomer). This was calculated by measuring the level of fluorescence of the Alexa conjugated p(AAc) and fitting a linear relationship between fluorescence and p(AAc) concentration, and correlating this to a standard curve of fluorescence vs Alexa concentration, to get a ratio of moles of Alexa to p(AAc) in the conjugated product.

A sIPN hydrogel was then prepared with the 450,000 MW p(AAc) linear chains that had been conjugated with Alexa. Briefly, dry nitrogen gas was bubbled through a mixture of 2.435 g (0.0215 mol) of NIPAAm, 0.065 g (0.903 mmol) of AAc, 0.005 g (0.0325 mmol) of N,N'-methylenebis(acrylamide), and 0.005 g of the Alexa conjugated p(AAc), and 50 mL of PBS in a covered one necked flask for 15 min. Following the nitrogen gas purge, 0.020 g (0.0876 mmol) of ammonium peroxydisulfate and 200 µL (0.0013 mol) of N,N,N',N'-tetramethylethylenediamine were added as the initiator and accelerator, respectively. The mixture was stirred vigorously for 20 s and allowed to polymerize under light at RT (~25° C.) for 19 hr in a 250 mL glass beaker covered with a glass plate. Following polymerization, the sIPN hydrogel was washed for 20 min three times in UP water to extract unreacted compounds. From the substitution efficiency calculation, this gives an Alexa concentration in the sIPN of 8.1×10$^{-7}$ mol/ml.

Figure 4:
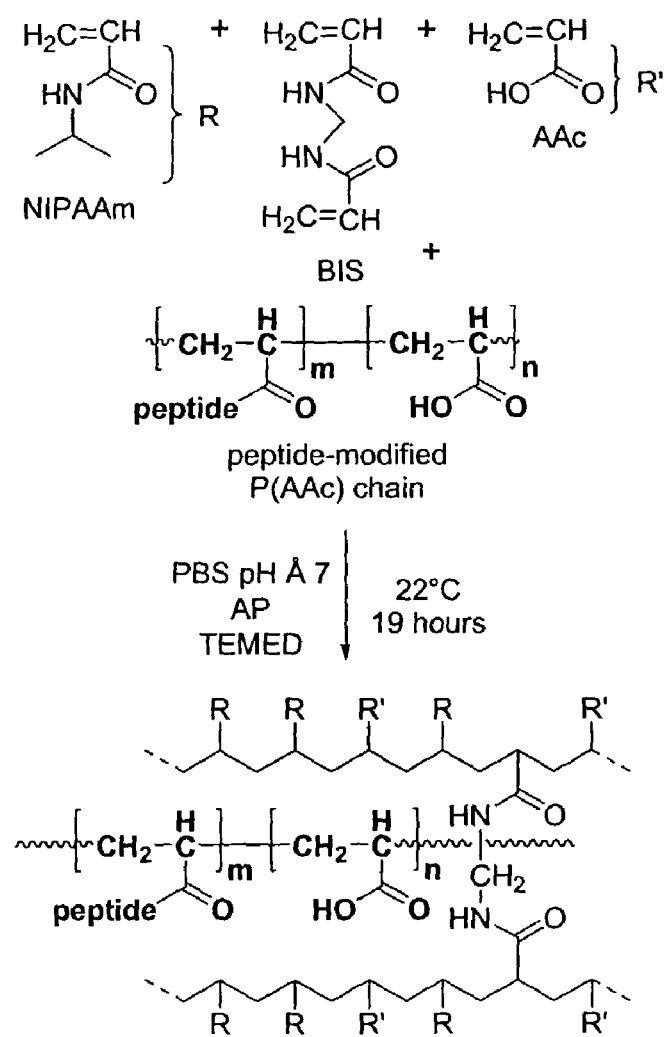
FIG. 4 is a synthetic scheme for preparing a s-IPN of the invention, which incorporates a peptide-modified linear p(AAc) polymer. The modified p(AAc) chains are added to the polymerization formulation, and the p(NIPAAm-co-AAc) cross-linked network forms in the presence of the chains. Thus, the chains are physically entangled within the network.

This gave the Alexa-sIPN red UV fluorescence (599 nm emission peak), and a distinct pink color to the eye. The hydrogel was placed on a glass slide, and small volumes (~10 µl) of a concentrated suspension of EGFP expressing cells derived from mouse bone marrow were pipetted onto it. These were mixed with the gel via agitation with a syringe needle, and manipulation with a slide cover slip. The gel was then aspirated into a 1 cc syringe. The results are shown in FIG. 4, where the bright circles in the combined fluorescent image represent the mixture of the sIPN with EGFP expressing bone marrow derived cells.

2.3 Hydrogel Injection

Figure 5:
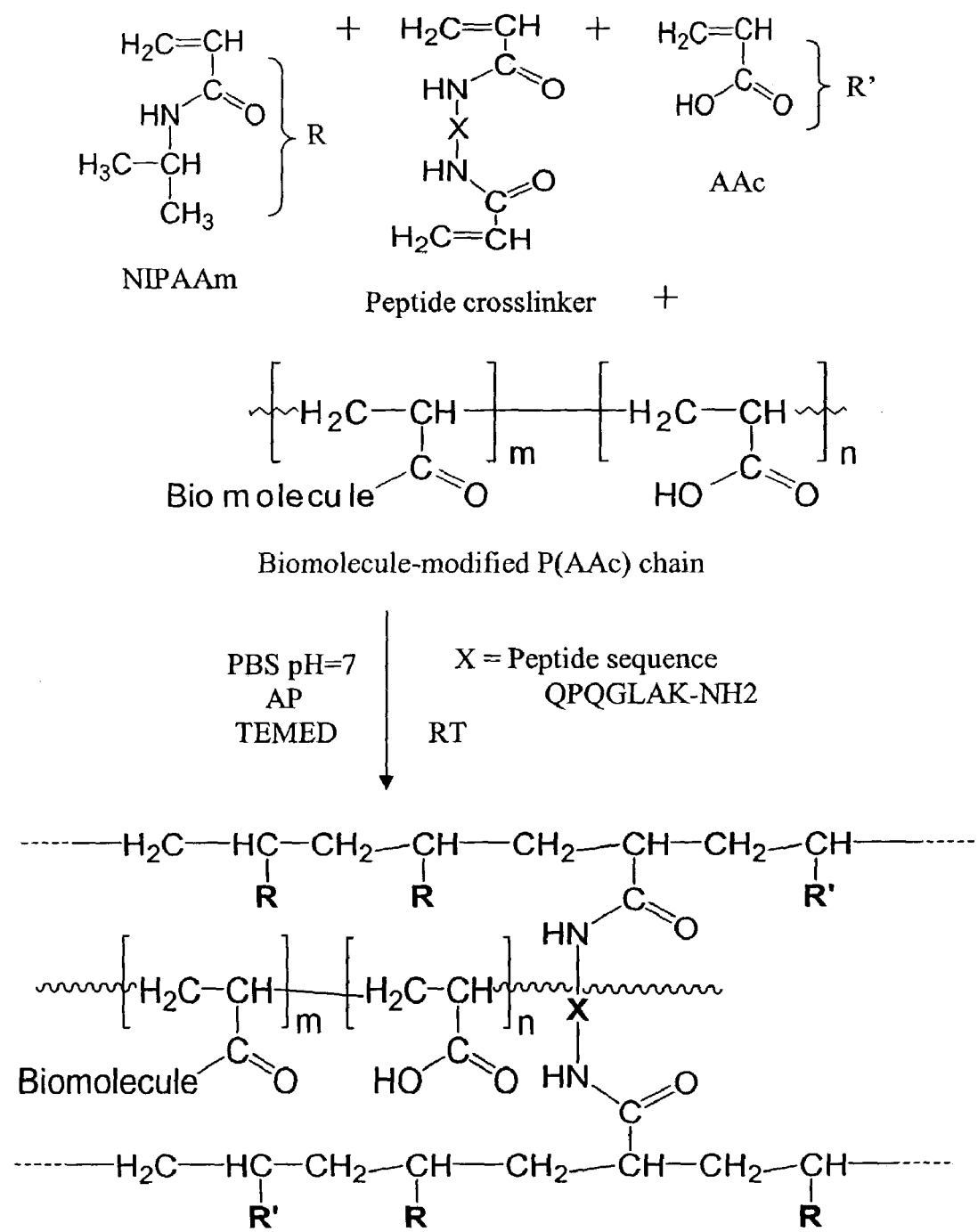
FIG. 5 is a synthetic scheme for preparing a s-IPN of the invention, which incorporates a modified linear p(AAc) polymer and has an protease degradable cross-linker. The modified p(AAc) chains are added to the polymerization formulation, and the p(NIPAAm-co-AAc) protease cross-linked network forms in the presence of the chains. Thus, the chains are physically entangled within the network.

An adult female C57BL/6 mouse was anaesthetized with isoflurane, its chest was opened, and its thigh was prepared for injection. Fluorescently conjugated hydrogel (~100 µl per injection) was injected into the ventricle walls and thigh muscles through a 30 gauge needle. The heart and muscles were then excised, and placed in OCT solution before being plunged into liquid nitrogen and preserved at −80° C. Cryosections were prepared from these organs at 10 µm thickness, and were not fixed or stained. Some macroscopic fracture of tissue caused by this technique was observed. Injection of hydrogel into the myocardium of a beating heart was observed during the procedure by the investigators and was confirmed by histological short axis cross sections. The results are shown in FIG. 5, where the fluorescent image shows the sIPN location (light) in the mouse myocardial tissue (dark).

Example 3

To synthesize a peptide crosslinker that is cleaved by matrix metalloproteinases (e.g. MMP-13), the peptide sequence Gln-Pro-Gln-Gly-Leu-Ala-Lys-NH2 (QPQGLAK-NH2) (SEQ ID NO: 4) was utilized as an example. QPQGLAK-NH2 (SEQ ID NO: 4) was characterized by mass spectrometry, and its purity was determined by reversed phase high performance liquid chromatography (RP-HPLC). A peptide crosslinker with bifunctional acryl groups was synthesized through the reaction between the amine groups of glutamine and lysine residues in the peptide sequence and acryloyl chloride (West, J. L.; Hubbell, J. A. Macromolecules 1999, 32, 241-244: Loudon, G. M. Organic Chemistry, 3rd ed.; Benjamin/Cummings Publishing Company, Inc., 1995) This produced an amide linkage between the peptide and the acrylic group. Specifically, 30 mg of peptide was dissolved in 1.2 ml of dimethylacetamide (DMAc) with triethylamine, and acryloyl chloride solution was added dropwise to the solution with stirring. The reaction temperature was kept at 0-5° C. After all the acryloyl chloride was added, the reaction continued with stirring for 4 h at 0-5° C. and 20 h at room temperature. Subsequently, triethylamine hydrochloride salts were removed by filtration. The resulting solution was dialyzed against ultrapure water (UPW; 18 MΩ-cm) for 48 h with periodic bath changes to remove unreacted compounds. The final dialysis product was lyophilized overnight using a freeze dryer (VIRTIS, Gardiner, N.Y.) attached with vacuum pump (Edwards, RV12).

3.1 Synthesis of Peptide-Crosslinked sIPNs P(NIPAAm-co-AAc) Hydrogels

The loosely crosslinked P(NIPAAm-co-AAc) hydrogels were prepared with the peptide crosslinker by redox polymerization in aqueous media. The method used to synthesize degradable semi-IPNs composed of P(NIPAAm-co-AAc) and linear poly(acrylic acid) [P(AAc)] chains (average MW 450,000 g/mol) was similar to that published previously (Stile, R. A.; Burghardt, W. R.; Healy, K. E. Macromolecules 1999, 32, 7370-7379: Stile, R. A.; Healy, K. E. Biomacromolecules 2001, 2, 185-194: Stile, R. A.; Healy, K. E. Biomacromolecules 2002, 3, 591-600). The hydrogels were prepared by varying the molar ratio of NIPAAm/AAc and the amount of peptide crosslinker in the feed. The total monomer amount of NIPAAm and AAc in the feed was always 5 w/v %, and the NIPAAm/AAc molar ratios of 96/4, 96.5/3.5 and 97/3 were used. The amount of poly(acrylic acid) [P(AAc)] chains (average MW 450,000 g/mol) was also varied from $5.45 \times 10^{-5}$ to $1 \times 10^{-4}$ mole %. Dry nitrogen gas was bubbled through a mixture of NIPAAm, AAc, peptide crosslinker, and p(AAc) in phosphate-buffered saline (PBS) in a flask for 15 min to remove dissolved oxygen. Following the nitrogen gas purge, 0.8 wt % (based on total monomer) of ammonium peroxysulfate (AP) and 8 v/w % (based on total monomer) of N,N,N',N'-tetramethylethylenediamine (TEMED) was added as the initiator and accelerator, respectively. The mixture was stirred vigorously for 15 s and allowed to polymerize at room temperature for 24 h under regular fluorescent lighting in a glass vial. Following the polymerization, the peptide-crosslinked P(NIPAAm-co-AAc) hydrogel was washed three times, 15~20 min each, in excess ultrapure water to remove unreacted compounds.

Figure 6:
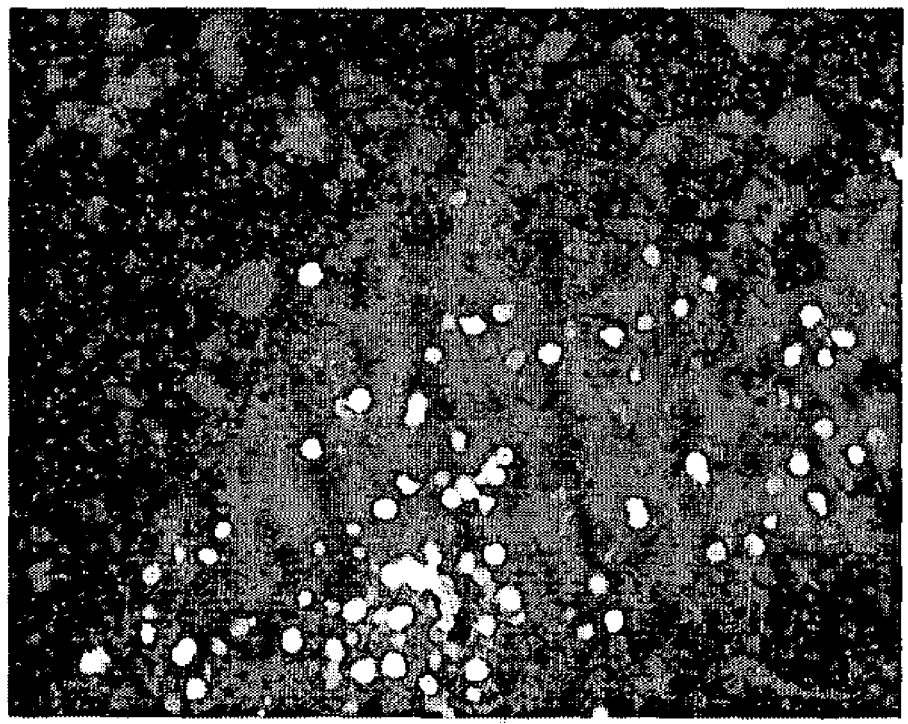
FIG. 6 is a fluorescent image of bone marrow derived cells. The bright circles in the image represent the mixture of the sIPN with the EGFP expressing bone marrow derived cells.
Figure 7:
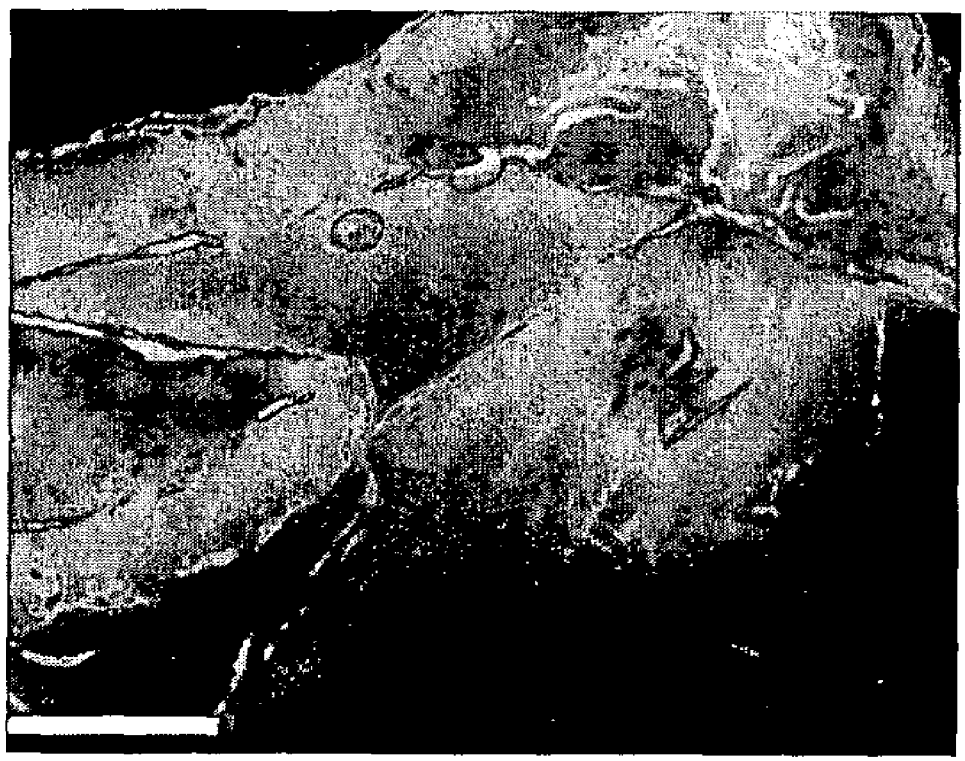
FIG. 7 is a fluorescent image of mouse myocardial tissue. The light sections of the image represent the sIPN location in the surrounding dark mouse myocardial tissue.
Figure 8:
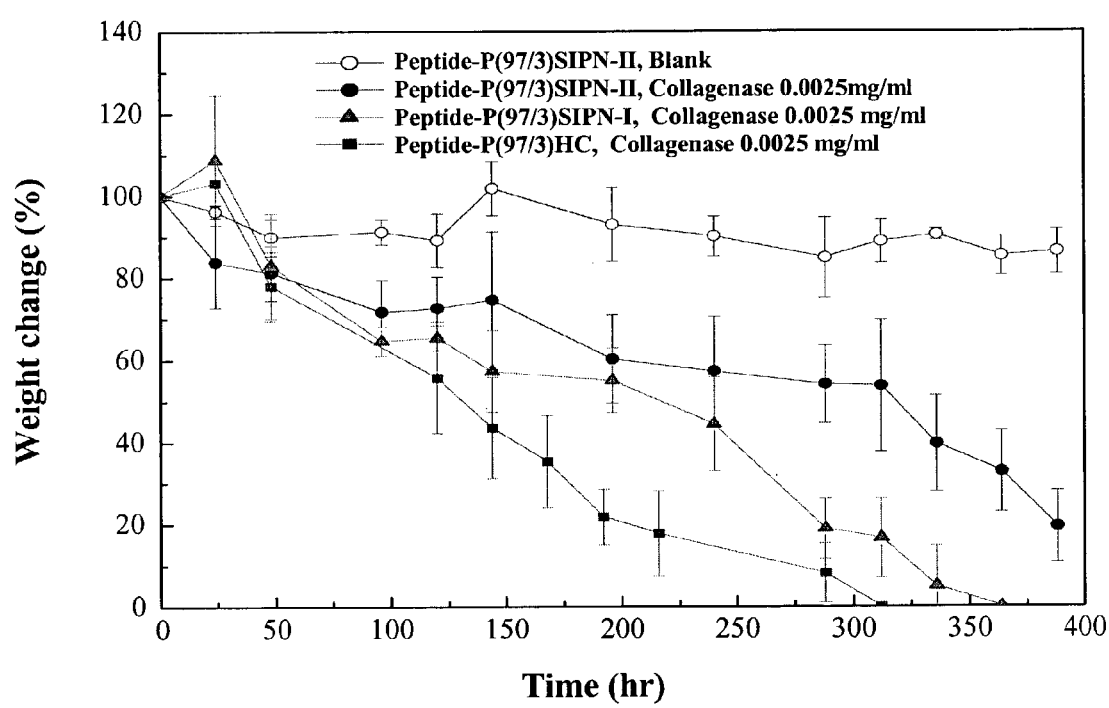
FIG. 8 is a graph of enzymatic degradation behavior as a function of time for peptide-crosslinked sIPN hydrogels by collagenase (0.0025 mg/ml). In this figure peptide-P(97/3) SIPN-I has $5.45 \times 10^5$ mol % of PAAc, peptide-P(97/3)SIPN-II has $1.09 \times 10^{-4}$ mol % of PAAc, and peptide-P(97/3)-HC hydrogels have the same network composition without any PAAc chains.

3.2 Enzymatic Degradation Behavior of Peptide-Crosslinked P(NIPAAm-co-AAc) Hydrogels To assess the enzymatic degradation of the peptide-crosslinked sIPN P(NIPAAm-co-AAc) hydrogels, the weight change kinetics were monitored as a function of exposure to two different enzymes: collagenase (from *Clostridium histolyticum*; EC number 3.4.24.3) and elastase (pancreatic solution from porcine pancreas; EC number 3.4.21.36). FIG. 6 exhibits the enzymatic degradation behavior as a function of time for peptide-crosslinked sIPN P((NIPAAm-co-AAc)97/3 hydrogels by collagenase (0.0025 mg/ml). In FIG. 6, peptide-P(97/3) sIPN-I has $5.45 \times 10^{-5}$ mol % of PAAc, peptide-P(97/3)SIPN-II has $1.09 \times 10^{-4}$ mol % of PAAc, and peptide-P(97/3)-HC hydrogels have the same network composition without any PAAc chains. The weight change kinetics for the peptide-crosslinked sIPN were greater than that of the hydrogels in the blank solution, thus indicating that the degradation of the peptide-P(NIPAAm-co-AAc)97/3-HC hydrogels was specifically dependent on collagenase, as designed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polymer network comprising:
   a cross-linked polymer, said cross-linked polymer-being a hydrogel; and
   a linear polymer, the polymer chains of which are entangled within said cross-linked polymer and derivatized with a bioactive molecule,
   wherein said linear polymer is not covalently bonded to said cross-linked polymer;
   said polymer network having an LCST (lower critical solution temperature) above room temperature and at or below mammalian body temperature.

2. The polymer network according to claim 1, wherein said bioactive molecule promotes interaction between a cell and said network.

3. The polymer network according to claim 1, wherein said bioactive molecule promotes interaction between a tissue and said network.

4. The polymer network according to claim 1, wherein said bioactive molecule promotes interaction between an extracellular matrix component and said network.

5. The polymer network according to claim 1, wherein said bioactive molecule is a therapeutic moiety.

6. The polymer network according to claim 1, wherein said bioactive molecule is a member selected from a functional protein, antigen, peptide, nucleic acid, lectin, receptor, saccharide, ganglioside and cerebroside.

7. The polymer network according to claim 6, wherein said peptide is a member selected from antibodies and enzymes.

8. The polymer network according to claim 1, wherein a cross-link in said cross-linked polymer is biodegradable.

9. The polymer network according to claim 1, wherein said bioactive molecule is attached to said linear polymer via a biodegradable linker.

10. The polymer network according to claim 1, wherein said cross-linked polymer comprises a subunit derived from N-isopropylacrylamide.

11. The polymer network according to claim 10, wherein said cross-linked polymer is poly(N-isopropylacrylamide).

12. The polymer network according to claim 1, wherein said linear polymer derivatized with a bioactive molecule comprises a subunit functionalized with said bioactive molecule, said subunit derived from a member selected from hyaluronic acid, methacrylic acid, dimethylaminopropylacrylamide, 2-acrylamido-2-methylpropane sulphonic acid, ethylene glycol, lysine and copolymers thereof.

13. The polymer network according to claim 12, wherein said linear polymer derivatized with a bioactive molecule is polyacrylic acid in which at least one acrylic acid subunit is functionalized with said bioactive molecule.

14. The polymer network according to claim 1, further comprising:
   (c) a cell interacting with said network via said bioactive molecule.

15. The polymer network according to claim 14, wherein said cell is a member selected from osteoblasts, bone marrow stem cells, mesenchymal stem cells, cardiac myocytes, and articular chondrocytes.

16. The polymer network according to claim 1, wherein said linear polymer is a member selected from hyaluronic acid, poly(methacrylic acid), poly(ethylene glycol), poly(l-ysine), poly(dimethylaminopropylacrylamide) and poly(2-acrylamido-2-methylpropane sulphonic acid).

17. The polymer network according to claim 1, wherein said linear polymer is a member selected from a copolymer and a terpolymer.

18. The polymer network according to claim 12, wherein said linear polymer derivatized with a bioactive molecule comprises a subunit functionalized with said bioactive molecule, said subunit derived from a member selected from hyaluronic acid, methacrylic acid, dimethylaminopropylacrylamide, 2-acrylamido-2-methylpropane sulphonic acid, ethylene glycol, lysine and copolymers thereof.

19. The polymer network according to claim 18, wherein said linear polymer derivatized with a bioactive molecule is polyacrylic acid in which at least one acrylic acid subunit is functionalized with said bioactive molecule.

20. The polymer network according to claim 18, wherein said linear polymer derivatized with a bioactive molecule is polyacrylic acid in which at least one acrylic acid subunit is functionalized with said bioactive molecule.

21. The polymer network according to claim 18, further comprising:
   (c) a cell interacting with said network via said bioactive molecule.

22. The polymer network according to claim 21, wherein said cell is a member selected from osteoblasts, bone marrow stem cells, mesenchymal stem cells, cardiac myocytes, and articular chondrocytes.

23. The polymer network according to claim 1, wherein said cross-linked polymer is thermo-responsive.

24. The polymer network according to claim 1, wherein said polymer network becomes more rigid when heated from room temperature to body temperature.

25. The polymer network according to claim 1, wherein said cross-linked polymer comprises a subunit derived from N-alkyl-acrylamide.

26. The polymer network according to claim 1, wherein said cross-linked polymer is derived from a non-cross-linked monomer and a cross-linking agent.

27. The polymer network according to claim 1, wherein said semi interpenetrating polymer network is a product of a process comprising the steps of:
   derivatizing said linear polymer with said bioactive molecule;
   contacting the product of step (a) and a monomeric precursor of said cross-linked polymer and a cross-linking agent; and
   initiating polymerization of said monomeric precursor,
thereby forming said semi interpenetrating polymer network.

28. The polymer network according to claim 1, wherein said linear polymer comprises linear polymer chains, wherein each of said linear polymer chains is derivatized with said bioactive molecule.

29. The polymer network according to claim 6, wherein said bioactive molecule is an adhesion peptide.

30. The polymer network according to claim 29, wherein said adhesion peptide is selected from an RGD peptide and a FHRRIKA (SEQ ID NO: 3) peptide.

* * * * *